United States Patent [19]

Guarino

[11] 4,188,404

[45] Feb. 12, 1980

[54] TREATMENT OF SYMPTOMS OF AGING

[75] Inventor: Richard A. Guarino, Glen Ridge, N.J.

[73] Assignee: USV Pharmaceutical Corporation, Tuckahoe, N.Y.

[21] Appl. No.: 914,339

[22] Filed: Jun. 12, 1978

[51] Int. Cl.$^2$ .......................................... A61K 31/135
[52] U.S. Cl. ................................................... 424/330
[58] Field of Search ......................................... 424/330

[56] References Cited
PUBLICATIONS

Treptow et al., Arch. of Neurology, 9:142, pp. 52–56, 1963.

Primary Examiner—Stanley J. Friedman
Attorney, Agent, or Firm—Leon E. Tenenbaum

[57] ABSTRACT

Nylidrin administered to institutionalized patients who are over 65 years of age and demonstrate a mild to moderate severity in cognitive, emotional and physical symptoms of the SCAG rating, produced significant improvement.

2 Claims, No Drawings

TREATMENT OF SYMPTOMS OF AGING

This invention relates to the relief of symptoms of aging. It particularly relates to the use of the compound, p-hydroxy-N-(1-methyl-3phenylpropyl)-norephedrine (hereinafter referred to as "nylidrin") in such relief.

Because of the assumption that arteriosclerotic patients would benefit from improved cerebral circulation, vasodilators such as tolazoline hydrochloride and 3-pyridinemethanol have had extensive clinical use. It has, however, been established that these agents do not increase cerebral blood flow (Circulation 1:1148, 1950).

Later work with the vasodilator, isoxuprine hydrochloride, demonstrated its effectiveness in increasing cerebral blood flow (Wien Klin. Wschr. 70:145, 1958). Further studies of this drug indicated a small, but significant, improvement in performance on psychological tests, but no behavioral improvement in regard to self care and social responsibility (J. Nerv. Ment. Dis. 132:335, 1961).

Previous studies with another vasodilator, nylidrin, have shown some improvement in intellectual performance on Digit Span and Block Design Tests, but no corresponding improvements in adjustment to hospital routine could be demonstrated (Arch. of Neurology 9:142, 1963).

It is, accordingly, an object of the present invention to provide alleviation of cognitive, emotional and physical symptoms in the aged patient.

It is another object of the present invention to provide such alleviation as assessed by the Sandoz Clinical Assessment-Geriatric (SCAG) rating as described in the Journal of the American Geriatrics Society Vol. XXII, No. 3, March 1974.

It has now been found that nylidrin, a compound described in U.S. Pat. Nos. 2,661,372 and 2,661,373, has a pronounced effect in the alleviation of cognitive, emotional and physical symptoms in aged patients as measured by the SCAG rating.

The studies demonstrating this effect of nylidrin were double blind and placebo controlled on institutionalized patients over 65 years of age who, before being admitted to the study, demonstrated at least a mild to moderate degree of severity on six (6) or more of the eighteen (18) characteristics relating to cognitive, emotional and physical symptoms in the SCAG rating. The patients to whom nylidrin was administered received from 3 mg. to 24 mg. daily.

Nylidrin was prepared according to the methods described in U.S. Pat. Nos. 2,661,372 and 2,661,373 and was used as a salt, preferably the hydrochloride salt, in tablets containing 6.3 mg. of the salt, equivalent to about 6 mg. free nylidrin base.

Each nylidrin scored tablet contained:

| | |
|---|---|
| Nylidrin HCl | 6.300 mg. |
| Gelatin USP (150 Bloom) | 1.240 mg. |
| Gum acacia Powder USP | 1.240 mg. |
| Bottlers Sugar or Granulated Sugar | 6.000 mg. |
| Powdered Sugar 12X or Microfine | 30.840 mg. |
| Lactose Impalpable Powder USP | 30.840 mg. |
| Starch USP | 4.050 mg. |
| Magnesium Stearate | 0.610 mg. |

The matching placebos were of identical appearance and taste and each placebo tablet contained:

| | |
|---|---|
| Gelatin USP (150 Bloom) | 1.240 mg. |
| Gum Acacia Powder USP | 1.240 mg. |
| Bottlers Sugar or Granulated Sugar | 6.000 mg. |
| Powdered Sugar 12X or Microfine | 30.840 mg. |
| Lactose Impalpable Powder USP | 37.140 mg. |
| Starch USP | 4.050 mg. |
| Magnesium Stearate USP | 0.610 mg. |

The results of the studies indicated statistically significant improvement on the SCAG rating after the administration of nylidrin. No such results were obtained with the placebo.

The nylidrin may be used as a free base or as a pharmaceutically acceptable, non-toxic acid addition salt such as, for example, the hydrochloride, phosphate, sulfate, lactate, acetate, benzoate, citrate and the like. The compound may be administered orally in the form of tablets, capsules, lozenges or syrups, in effective daily dosages ranging from about 3 to 24 mg. per day. Obviously, the physician will ultimately determine the dosage which will be most suitable for a particular individual.

Examples 1-6 describe the preparation of various pharmaceutical dosage forms suitable for oral administration.

Example 1

| Ingredients | Quantity |
|---|---|
| 1. Nylidrin HCl, NF | 60 g. |
| 2. Lactose, USP | 600 g. |
| 3. Microcrystalline Cellulose, NF | 134 g. |
| 4. Directly compressible Starch | 200 g. |
| 5. Magnesium Stearate, USP | 6 g. |
| | 1000 g. |

Method of Preparation:
A. Blend 1, 2, 3, and 4. Pass through a #30 mesh screen.
B. Add 5 and blend.
C. Compress into 9/32' tablets using a suitable tablet press to obtain about 10,000 mg. scored tablets.

Example 2

| Ingredients | Quantity |
|---|---|
| 1. Nylidrin HCl, NF | 120 g. |
| 2. Lactose, USP | 870 g. |
| 3. Microcrystalline Cellulose, NF | 200 g. |
| 4. Directly compressible Starch | 300 g. |
| 5. Magnesium Stearate, USP | 10 g. |
| | 1500 g. |

Method of Preparation:
A. Blend 1, 2, 3, and 4. Pass through a #30 mesh screen.
B. Add 5 and blend.
C. Compress into 5/16' tablets using a suitable tablet press to obtain about 10,000 12 mg. scored tablets.

Example 3

| Ingredients | Quantity |
|---|---|
| 1. Nylidrin HCL | 6 g. |
| 2. Lactose, USP | 193 g. |
| 3. Magnesium Stearate, USP | 1 g. |
| | 200 g. |

Method of Preparation:
A. Suitable blend 1 with a small portion of 2. Pass through a #40 mesh screen.
B. Blend Step A mixture with the remainder of 2.
C. Add 3 and blend.
D. Encapsulate the blend in 1000 #4 two-piece hard gelatin capsules which contain 6 mg. each.

Example 4

| | Ingredients | Quantity |
|---|---|---|
| 1. | Nylidrin HCL | 12.0 g. |
| 2. | Lactose, USP | 286.5 g. |
| 3. | Magnesium Stearate, USP | 1.5 g. |
| | | 300.0 g. |

Method of Preparation:
A. Suitable blend 1 with a small portion of 2. Pass through a #4 mesh screen.
B. Blend step A mixture with the remainder of 2.
C. Add 3 and blend.
D. Encapsulate the blend in 1000 #3 two-piece hard gelatin capsules which contain 12 mg. each.

Example 5

| | Ingredients | Quantity |
|---|---|---|
| 1. | Nylidrin HCl, Nf | 1.2 g. |
| 2. | Sodium Benzoate, USP | 1.0 g. |
| 3. | Saccharin Sodium, NF | 0.5 g. |
| 4. | Glycerin | 50.0 ml. |
| 5. | Sorbitol Solution 70%, USP | 100.0 ml. |
| 6. | Sugar, granulated | 500.0 g. |
| 7. | FD&C Yellow No. 6 | 0.1 g. |
| 8. | Imitation Orange Flavor | 5.0 ml. |
| 9. | Water, Purified, USP qs to | 1000.0 ml. |

This composition contains 6.0 mg. of Nylidrin HCl per 5 ml. of syrup.

Method of Preparation:
A. Dissolve 1 in about 300 ml. of 9 with agitation.
B. Continue agitation and dissolve 2, 3, and 6 in the batch.
C. Add 4 and 5 and mix until the batch is homogeneous.
D. In a separate container, dissolve 7 in about 10 ml. of 9, and add this solution into the batch mix.
E. Add 8 and bring the batch to volume with 9.
F. Mix until the batch is homogeneous.
G. Filter through a suitable filter press.

Example 6

| | Ingredients | Quantity |
|---|---|---|
| 1. | Nylidrin HCl, NF | 2.4 g. |
| 2. | Sorbitol Solution 70%, USP | 80.0 g. |
| 3. | Glycerin, USP | 20.0 g. |
| 4. | Methylparaben, USP | 1.5 g. |
| 5. | Propylparaben, USP | 0.5 g. |
| 6. | Sodium Citrate (dihydrate), USP | 5.0 g. |
| 7. | Sugar, granulated | 150.0 g. |
| 8. | FD&C Red No. 4 | 0.1 g. |
| 9. | Imitation Cherry Flavor | 4.0 mg. |
| 10. | Water, Purified, USP qs to | 1000.0 ml. |

This composition contains 12.0 mg. of Nylidrin HCl per 5 ml. of syrup.

Method of Preparation:
A. Dissolve 1 in about 500 ml. of 10 with agitation.
B. Continue agitation and dissolve 6 and 7.
C. Add 2 and 3 and mix until the batch is homogeneous.
D. In a separate container, dissolve 4 and 5 in about 100 ml. of hot (80°) 10. Add to the batch.
E. Prepare separately a solution of 8 in about 10 ml. of 10 and add to the batch. Mix.
F. Add 9 to the batch and bring to volume with 10. Mix until homogeneous.
G. Filter through a suitable filter press.

I claim:
1. A method for improving the Sandoz Clinical Assessment-Geriatric rating in aged patients which comprises orally administering to aged patients requiring such improvement an effective amount of nylidrin hydrochloride.
2. A method according to claim 1 wherein the amount is about 3 to 24 mg. administered daily.

* * * * *